United States Patent [19]

Pera

[11] Patent Number: 5,051,124

[45] Date of Patent: Sep. 24, 1991

[54] MICROBICIDAL COMPOSITIONS OF DIMETHYLAMINE-EPICHLOROHYDRIN AMINES

[75] Inventor: John D. Pera, Cordova, Tenn.

[73] Assignee: Buckman Laboratories International, Inc., Memphis, Tenn.

[21] Appl. No.: 425,913

[22] Filed: Oct. 24, 1989

[51] Int. Cl.[5] ............................................. A01N 33/04
[52] U.S. Cl. ........................................ 71/67; 514/642
[58] Field of Search ............................ 71/67; 514/642

[56] References Cited

U.S. PATENT DOCUMENTS

| | | | |
|---|---|---|---|
| Re. 28,807 | 5/1976 | Panzer et al. ...................... | 528/405 |
| Re. 28,808 | 5/1976 | Panzer et al. ...................... | 528/405 |
| 3,738,945 | 6/1973 | Panzer et al. ...................... | 210/736 |
| 3,894,944 | 7/1975 | Panzer et al. ...................... | 210/736 |
| 3,894,945 | 7/1975 | Panzer et al. ...................... | 210/736 |
| 3,894,946 | 7/1975 | Panzer et al. ...................... | 210/736 |
| 3,894,947 | 7/1975 | Panzer et al. ...................... | 210/736 |
| 3,930,877 | 1/1976 | Aitken ............................... | 210/728 |
| 3,975,347 | 8/1976 | Phillips et al. ...................... | 524/800 |
| 4,104,161 | 8/1978 | Wein .................................. | 210/736 |
| 4,111,679 | 9/1978 | Shair et al. ........................ | 71/67 |
| 4,140,798 | 2/1979 | Merianos et al. .................. | 514/667 |
| 4,147,627 | 4/1979 | Godman ............................ | 210/698 |
| 4,164,521 | 8/1979 | Goodman .......................... | 528/187 |
| 4,166,041 | 8/1979 | Goodman .......................... | 252/180 |
| 4,606,773 | 8/1986 | Novak ................................ | 106/213 |
| 4,769,155 | 9/1988 | Dwyer .............................. | 210/728 |

Primary Examiner—Richard L. Raymond
Assistant Examiner—Brian M. Burn
Attorney, Agent, or Firm—Finnegan, Henderson, Farabow, Garrett & Dunner

[57] ABSTRACT

A method of inhibiting the growth and proliferation of microorganisms by the use of a polymeric quaternary ammonium composition is provided. The composition is prepared by reacting dimethylamine and a polyfunctional amine with epichlorohydrin.

16 Claims, No Drawings

MICROBICIDAL COMPOSITIONS OF DIMETHYLAMINE-EPICHLOROHYDRIN AMINES

FIELD OF THE INVENTION

This invention relates to the use of polymeric quaternary ammonium compositions, also referred to as ionene polymers, which have been prepared by the reaction of epichlorohydrin with mixtures of dimethylamine and a polyfunctional amine for the control of microorganisms, e.g., bacteria and algae. The products of this invention are useful as bactericides and algicides in swimming pools and in aqueous systems in industrial and commercial installations employing water as the major component. The bactericides/algicides of the invention are substantially nonfoaming and nonirritating to humans, animals, and fowl.

BACKGROUND OF THE INVENTION

Quaternary ammonium compounds and linear polymeric quaternary ammonium compounds are used to eliminate or inhibit the growth of bacteria and algae in fresh water supplies used in commercial and industrial operations, in cooling water used for many types of systems, and in swimming pools. The polymeric products are generally prepared by the reaction of dihalo compounds with ditertiary amines, and the molecular weights of the polymers are usually low and in the area of less than 10,000. The products of the reaction of dimethylamine with epichlorohydrin are also low molecular weight polymers that are effective against bacteria and algae in aqueous systems. Higher molecular weight polymers have generally been used as flocculants. It is generally recognized that the lower molecular weight polymers will have a higher toxicity to humans, animals and fish than the higher molecular weight products.

Panzer and Dixon obtained U.S. Pat. No. 3,738,945 and Reissue U.S. Pat. No. 28,807, which disclose a water dispersible polyquaternary polymer of essentially linear structure made from dimethylamine and epichlorohydrin. Later patents disclose processes for clarifying raw water using the polymers described by Panzer and Dixon. See U.S. Pat. No. 3,894,944. U.S. Pat. No. 3,894,947 covers the use of dimethylamine-epichlorohydrin polymers for flocculating industrial wastes. U.S. Pat. No. 3,975,347 relates to a process for the preparation of a 60 to 85% aqueous solution of a linear dimethylamine-epichlorohydrin polymer. U.S. Pat. No. 4,111,679 discloses a method for controlling microorganisms in industrial cooling water systems which comprises adding to the system a microbicidal amount of a polyquaternary amine of the formula

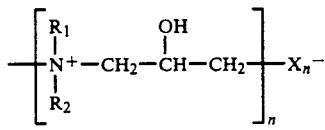

where $R_1$ and $R_2$ are methyl or ethyl, X is Cl, Br, or I and n is from 3 to 10,000. The patentee states that the polyamines are made by reacting dimethylamine with epichlorohydrin as described in U.S. Pat. No. 3,738,945.

Another patent, U.S. Pat. No. 4,140,798, discloses a method of inhibiting microorganisms using a compound formed by the condensation of dimethylamine and epichlorohydrin in about a 1:1 molar ratio. Uses listed in the specification are recirculating water systems, such as paper mills, air conditioners, humidifiers, grinding lubricants, swimming pools and other uses.

All of the patents referring to the use of dimethylamine-epichlorohydrin polymers as microbicides refer to linear polymers. Even though the original Panzer and Dixon patent (U.S. Pat. No. 3,738,945) discloses cross-linked polymers, no mention is made of these polymers as possessing antimicrobial properties. When the original patent, U.S. Pat. No. 3,738,945, was reissued the linear polymers were included in Reissue U.S. Pat. No. 28,807, but the cross-linked polymers were included in Reissue U.S. Pat. No. 28,808. This latter Reissue lists the coreactants with dimethylamine and epichlorohydrin as ammonia, primary amines, alkylenediamines, such as ethylenediamine; polyethylenepolyamines, such as diethylenetriamine, triethylenetetramine, etc.; polyglycolamines, piperazines, heteroaromatic diamines, and aromatic diamines. The amount of the polyfunctional amines listed above is up to about 15 mole percent of the total moles of the dimethylamine, and the total of all amines is at least equimolar to the epichlorohydrin. U.S. Pat. No. 3,894,945 discloses a process for clarifying raw water with the polymers of Reissue U.S. Pat. No. 28,808, and U.S. Pat. No. 3,894,946 relates a process for flocculating industrial wastes with the same polymers.

Additional uses for the cross-linked polymers have been patented since 1975. These are included in U.S. Pat. Nos. 3,930,877, 4,104,161, 4,164,521, 4,147,627, 4,166,041, 4,606,773 and 4,769,155. Usually the lower molecular weight linear ionene polymers have been used as microbicides.

SUMMARY OF THE INVENTION

It is a principal object of the present invention to provide a method of inhibiting the growth and proliferation of microorganisms, e.g., bacteria and algae, in an effective manner that is consistent with producing low toxicity to man and animals. It is another object of the present invention to provide a method as above for use in an aqueous system.

It is another object of the present invention to provide a method as above by the use of a cross-linked ionene type polymer that is inhibitory to the growth of microorganisms.

It is another object of the present invention to provide a method as above by the use of a higher molecular weight polymer that has a lower toxicity to man and animals than is currently being used to inhibit microbial growth in aqueous systems.

It is as yet another object of the present invention to provide a method as above by the use of a cross-linked ionene type polymer that is dispersible in aqueous systems.

In accomplishing these and other objectives of the present invention, there has been provided a method of inhibiting the growth and proliferation of microorganisms, such as algae and bacteria. In the method of the invention, microorganisms are contacted with a polymeric quaternary ammonium composition, referred to as an ionene polymer composition, which is characterized as a reaction product of dimethylamine, a polyfunctional amine that acts as a crosslinking agent, and epichlorohydrin. The ionene polymer composition contains repeating units of the structures

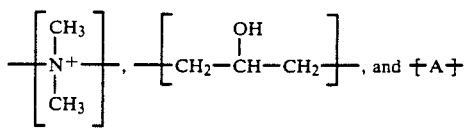 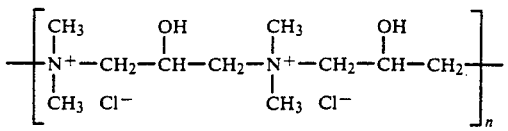

as the cationic portion of the polymer. The anionic portion is a either a bromide ion, Br⁻, or a chloride ion, Cl⁻. The

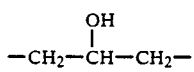

portion of the polymer is derived from the epichlorohydrin. The A structure is a residue obtained after at least bifunctional epoxy reaction from a polyfunctional amine selected from the group consisting of ammonia, primary amines, alkylene diamines of from 2 to 6 carbon atoms, polyethylenepolyamines, preferably selected from the group consisting of diethylenetriamine, triethylenetetramine, and tetraethylenepentamine, and polypropylenepolyamines.

The amount of the polyfunctional amine is from approximately 1 to 15 molar percent of the total moles of the dimethylamine and the polyfunctional amine. The amount of epichlorohydrin is from at least an equimolar quantity of the amines up to the full functional equivalency of the amines. The amount of the bromide or chloride ion present is that which is sufficient to satisfy the anion requirement of the cationic portion of the polyquaternary compound.

It was surprising to discover that cross-linked polymers as described in Reissue U.S. Pat. No. 28,808 had about the same outstanding effectiveness against bacteria and algae as the linear dimethylamine-epichlorohydrin polymers described in Reissue U.S. Pat. No. 28,807. The compositions of the invention comprise high molecular weight polymers of the type used as flocculants, but as applicant discovered, these polymers have outstanding effectiveness against microorganisms.

Further objects, advantages and features of the present invention will become apparent from the following detailed description. It should be understood, however, that the detailed description, while indicating preferred embodiments of the invention, is given by way of illustration only, since various changes and modifications within the spirit and scope of the invention will become apparent to those skilled in the art from this detailed description.

DETAILED DESCRIPTION OF THE INVENTION

When dimethylamine and epichlorohydrin are reacted, the linear polymer that results is as follows:

where n is about 4 to about 50. When a polyfunctional amine, such as methylamine or ammonia, is present in a low molar ratio relative to the epichlorohydrin, the polymer chain will have nitrogen atoms capable of further reaction. For example, an occasional methylamine molecule will produce a chain as follows:

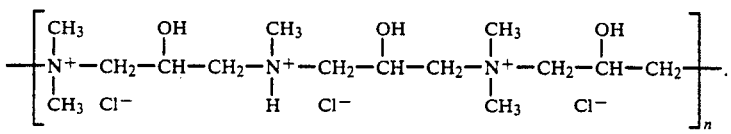

The portion of the polymer chain shown contains two fully reacted quaternary nitrogens and one tertiary amine nitrogen. The tertiary amine nitrogen is free to react with epichlorohydrin to form a branched chain. If too much polyfunctional amine is present, the polymer becomes an intractable gel that is useless in aqueous systems because it is insoluble in water.

The water dispersible or soluble higher molecular weight polymers are non-foaming in water, have a very low toxicity to humans and animals, and they retain their usefulness as flocculating agents. Low molecular weight linear polymers are not useful as flocculants. The higher molecular weight polymers are also easily removed from aqueous systems and will present no environmental hazards to fish and wildlife.

The products of this invention consist essentially of a reaction product of dimethylamine, a polyfunctional amine, and epichlorohydrin. The products comprise a polyquaternary polymer containing repeating units of the structures

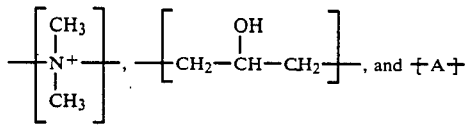

as the cationic portion, and Br⁻ or Cl⁻ as the anionic portion, wherein

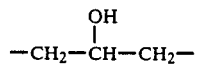

is derived from epichlorohydrin. A is a residue obtained after at least bifunctional epoxy reaction from a polyfunctional amine selected from the group consisting of ammonia, a primary amine, an alkylene diamine of from 2 to 6 carbon atoms, a polyethylenepolyamine, preferably selected from the group consisting of diethylenetriamine, triethylenetetramine, and tetraethylenepentamine, and a polypropylenepolyamine. The amount of the polyfunctional amine is from about 1 to about 15 molar percent of the total moles of the dimethylamine and the polyfunctional amine. The amount of epichlorohydrin is from at least about the equimolar quantity of the amines up to the full functional equivalency of the amines. The amount of the bromide or chloride ion present is sufficient to satisfy the anion requirement of the cationic portion of said polyquaternary compound.

The polyfunctional amines used should not be more than about 15% molar basis of the total molar amount of the dimethylamine and the polyfunctional amine, e.g., from about 1 to about 15%, but usually about 2 to about 8% molar basis will provide the desired result. Generally, lesser amounts of the polyamines with high functionality will be required. The quantities of polyamines must be carefully selected to prevent excessive cross-linking which may result in gel formation. The preferred primary amines are lower alkyl amines wherein the alkyl groups contain a maximum of three carbon atoms. The preferred diamines are ethylenediamine, propylenediamine, butylenediamine, and dimethylaminopropylamine.

It has been found that the ionene polymers of this invention provide excellent effectiveness against microorganisms, particularly bacteria and algae, in aqueous systems even at low concentrations. These polymers are readily soluble in water are non-foaming, and can be diluted to any desired concentration. Among the advantages of these polymers are long shelf life, lack of corrosiveness, and low toxicity to animals and humans.

The cross-linked ionene polymers of the present invention are useful in various types of aqueous systems. To mention a few, the ionene polymers can be employed in recirculating water systems, such as in paper mills, air conditioners, humidifiers, in metal working, e.g., as a grinding lubricant, and in swimming pools. The aqueous system in which the ionene polymers are employed can be fresh water, cooling water, or swimming pool water.

Concentrations of the ionene polymer that is suitable for the control of microorganisms vary from about 0.5 to about 500 parts per million (w/w), based upon the weight of the liquid being treated. When used in the paper mill industry in continuously operating recirculating water systems, the polymer can be added, preferably, to the water systems about every 12 hours, to a final concentration of about 0.5 to about 10 ppm (w/w). When used for swimming pools, the polymer can be employed, preferably, at a concentration of about 1 to about 20 ppm (w/w). When used in cooling waters in air conditioners and humidifiers, the polymer can be added to the water, preferably, initially as a single dose of from 1 to 100 ppm (w/w) and be replenished when the concentration falls below 5 ppm (w/w). When used in metal working, the polymer can be used at a concentration of about 50 to about 500 ppm (w/w), preferably, from about 100 to about 250 ppm (w/w).

The following Examples are given to facilitate a better understanding of the present invention. It is to be understood, however, that the Examples are given by way of illustration only and are not to be construed as limiting the invention in any way.

EXAMPLE 1

A one hundred gallon glass-lined reactor equipped with an agitator, suitable charging ports, and a heating-/cooling jacket was charged with 160 pounds of water, 122 pounds of a 60% dimethylamine solution, and 14 pounds of a 29% ammonia solution while keeping the temperature below 105° F. The reactor was sealed, and epichlorohydrin (150 pounds) was charged over a period of two hours while keeping the temperature below 105° F. using chilled water in the reactor jacket. When the temperature exceeded 105° F., the addition of epichlorohydrin was halted until the temperature dropped below 98° F. The mole ratio at this point was approximately 1:1:0.15 for epichlorohydrin/dimethylamine/ammonia.

The temperature was maintained at 100°–105° F. for one hour, and then the temperature was raised to 170°–175° F. using steam in the jacket. The pH at this point was 8.2; after ninety minutes at 170°–180° F., the pH was 7.5. Nine (9) pounds of 50% sodium hydroxide were added to bring the pH up to 8.2.

Epichlorohydrin was then charged at two pounds per increment with approximately fifteen minutes between each charge. The temperature was maintained between 170° and 180° F. Eight charges were made in which 16.2 pounds of epichlorohydrin were added to the reactor. The pH was adjusted from 7.4 to 7.75 by adding 6.7 pounds of 50% sodium hydroxide. After one hour at 170°–180° F., no increase in viscosity was apparent. The pH was then adjusted to 8.1 by adding 4.3 pounds of 50% sodium hydroxide.

Two more charges of epichlorohydrin, 2 pounds per charge, were made with thirty minutes between each charge. The viscosity then began to show an increase. At this point, the mole ratio of reactants was approximately 1.14:1:0.15 for epichlorohydrin/dimethylamine/ammonia. No more epichlorohydrin was added, and samples were obtained for viscosity measurement.

When Brookfield viscosity reached 1500 cP (at approximately 170° F.), 10 pounds of sulfuric acid were added to the reactor contents and cooling water was applied to the reactor jacket. The final product had a Brookfield viscosity at 3500 cP at room temperature. The polymer content was approximately 53%.

EXAMPLE 2

In the initial stage of the procedure, a one liter, three-neck, round bottom reaction flask equipped with a heating mantle, thermometer, condenser, agitator, and addition funnel was charged with 209.1 grams water. Two moles (150.2 grams) of a 60% aqueous dimethylamine solution and 0.1 moles (5.71 grams) of a 29.8% ammonia solution were charged to the flask while maintaining the temperature below 40° C. with an ice bath. Two moles (185 grams) of epichlorohydrin were weighed into the addition flask. The epichlorohydrin was charged to the reaction flask over a period of 90 minutes while maintaining the temperature below 40° C. using an ice bath.

The temperature was held between 40° and 45° C. for 30 minutes. The temperature was then raised to 80° C. The pH of the solution was measured and found to be 7.15. The pH was raised to 8.02 by charging 8.36 grams of a 50% solution of sodium hydroxide.

Following this initial stage of the procedure, a second part of the process involved charging additional epichlorohydrin until the contents of the flask became viscous. During the next 35 minutes, two separate charges of epichlorohydrin, 2 ml per charge, were added to the flask. At this time, the pH had dropped to 7.48. The pH was raised to 8.04 with 3.1 grams of 50% sodium hydroxide. Six more charges of epichlorohydrin, 2 ml per charge, were added to the contents of the flask during the next 225 minutes. The pH had dropped to 6.92 at the end of this period. The pH was raised to 8.03 with 3.4 grams of 50% sodium hydroxide. No more epichlorohydrin was added as the contents of the reactor became viscous. The total amount of epichlorohydrin charged was 2.18 moles, including the amounts added in each stage of the process. The molar ratio of the reactants was approximately 1.09:1:0:0.05 for epichlorohydrin/dimethylamine/ammonia.

The viscosity was monitored by drawing up 10 ml of hot solution into a pipet and measuring the time that it took for 5 ml of the hot solution to flow back into the flask. When this flow time exceeded 24 seconds, the reaction was stopped by adding 6.5 grams of sulfuric acid.

The final product had a pH of 2.51 and a Brookfield viscosity of 300 cP, both measured at 25° C. The polymer content was approximately 50%.

EXAMPLES 3-9

The procedure of Example 2 was followed with the same quantities of dimethylamine and epichlorohydrin charged at the beginning of the process, but with different quantities of ammonia and/or different crosslinking reagents as specified below. In each instance below, more epichlorohydrin was added following the initial part of the process until the contents of the flask became viscous. When the pH of the solution dropped below 7.5, the pH was raised to approximately 8.0 with 50% sodium hydroxide solution.

TABLE 1

| Ex No. | Moles of dimethylamine | Moles of epichlorohydrin (1st stage) | Crosslinking Agent | Moles of Crosslinking Agent | Moles of epichlorohydrin (2nd stage) |
|---|---|---|---|---|---|
| 3 | 2.0 | 2.0 | ammonia | 0.2 | 0.21 |
| 4 | 2.0 | 2.0 | ammonia | 0.3 | 0.21 |
| 5 | 2.0 | 2.0 | ammonia | 0.4 | 0.21 |
| 6 | 2.0 | 2.0 | methylamine | 0.2 | 0.28 |
| 7 | 2.0 | 2.0 | ethylenediamine | 0.2 | 0.19 |
| 8 | 2.0 | 2.0 | diethylenetetramine | 0.1 | 0.03 |
| 9 | 2.0 | 2.0 | dimethylaminopropylamine | 0.2 | 0.13 |

When the contents of the reaction flask became viscous, the reaction was stopped by the addition of sulfuric acid. In each instance the pH of the solution was adjusted to a point below 2.0. Products of these examples were then tested for biocidal effectiveness in the examples below. The polymer content in each instance was approximately 50%.

All of the polymers listed above in Examples 1-9 were analyzed by gel permeation chromatography. In each case, the weight average molecular weight was determined to be in excess of 100,000. By contrast, the linear polymer, i.e., a polymer made from epichlorohydrin and dimethylamine containing no cross-linking agent, was analyzed by the same procedure and the weight average molecular weight was determined to be less than 5,000.

EXAMPLE 10

The effect of the cross-linked ionene polymer described in Examples 1 to 8 on the percentage kill of the bacteria *Enterobacter aerogenes* and *Pseodomonas aeruginosa*, respectively, was determined using the method described in U.S. Pat. No. 2,881,070 with the modification described in U.S. Pat. No. 4,054,542. The results are included in Tables 2 and 3. The results are recorded in concentration in parts per million required for 80 percent kill or greater of the bacterium in a basal salt substrate after 18 hours contact. Concentrations are based upon approximately fifty percent solutions prepared in the Examples.

TABLE 2

| | *Enterobacter aerocenes* | |
|---|---|---|
| Polymers from Examples | pH 6.0–6.5 | pH 8.0–8.5 |
| 1 | 2.0 ppm | 2.0 ppm |
| 2 | 1.0 ppm | 1.0 ppm |
| 3 | 4.0 ppm | 0.5 ppm |
| 4 | 2.0 ppm | 0.5 ppm |
| 5 | 1.0 ppm | 1.0 ppm |
| 6 | 2.0 ppm | 0.5 ppm |
| 7 | 2.0 ppm | 0.5 ppm |
| 8 | 1.0 ppm | 1.0 ppm |

TABLE 3

| | *Pseudomonas aeruginosa* | |
|---|---|---|
| Polymers from Examples | pH 6.0–6.5 | pH 8.0–8.5 |
| 1 | 2.0 ppm | 2.0 ppm |
| 2 | 2.0 ppm | 2.0 ppm |
| 3 | 2.0 ppm | 4.0 ppm |
| 4 | 2.0 ppm | 2.0 ppm |
| 5 | 2.0 ppm | 4.0 ppm |
| 6 | 2.0 ppm | 4.0 ppm |
| 7 | 4.0 ppm | 2.0 ppm |
| 8 | 2.0 ppm | 2.0 ppm |

EXAMPLE 11

The effects of the cross-linked ionene polymers described in Examples 1 to 8 on the inhibition of algae *Chlorella pyrenoidosa*, *Chlorococcum hypnosporum*, and *Phormidium inundatum* was determined using the procedure described in Example 2 of U.S. Pat. No. 3,771,989. The results are included in Table 4. Concentrations are based on the approximately fifty percent solutions prepared in the Examples.

TABLE 4

| | Concentration in parts per million required for complete inhibition of growth after 28 days | | |
|---|---|---|---|
| Polymers From Example | *Chlorella pyrenoidosa* | *Chlorococcum hypnosporum* | *Phormidium inundatum* |
| 1 | 2.0 | 2.0 | 25.0 |
| 2 | 2.0 | 2.0 | 10.0 |
| 3 | 2.0 | 2.0 | 25.0 |
| 4 | 2.0 | 2.0 | 10.0 |
| 5 | 2.0 | 6.0 | 10.0 |
| 6 | 4.0 | 8.0 | 25.0 |
| 7 | 2.0 | 6.0 | 25.0 |
| 8 | 2.0 | 2.0 | 25.0 |

It is therefore apparent that the crosslinked ionene polymers of the present invention provide an unexpected method of inhibiting the growth and proliferation of algae and bacteria. The examples display that the crosslinked ionene polymer composition provides control of bacteria and algae at very low concentrations. A significant advantage of the crosslinked ionene polymers of the present invention is the low toxicity to humans from such compositions in comparison to the linear ionene polymer systems presently employed in industry.

What is claimed is:

1. A method of inhibiting the growth and proliferation of microorganisms comprising:

contacting said microorganisms with an amount of a polymeric quaternary ammonium composition that is effective to inhibit the growth and proliferation of a microorganism, wherein said composition comprises a crosslinked reaction product of dimethylamine, a polyfunctional amine, and epichlorohydrin, said composition containing repeating units of the structures

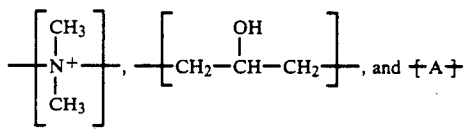

as a cationic portion of said composition, and Br⁻ or Cl⁻ as an anionic portion of said composition;

wherein A is a residue obtained after at least bifunctional epoxy reaction from a polyfunctional amine, and wherein the amount of said polyfunctional amine is from about 1 percent up to about 15 percent of the total moles of said dimethylene and said polyfunctional amine, and the amount of said epichlorohydrin is from at least about the equimolar quantity of said amines up to the full functional equivalency of said amines; and wherein the said bromide or chloride ion is present in an amount sufficient to satisfy the anion requirement of the cationic portion of said polymeric quaternary ammonium composition.

2. The method of claim 1, wherein said polyfunctional amine is selected from the group consisting of ammonia, a primary amine, an alkylene diamine of from 2 to 6 carbon atoms, a polypropylenepolyamine and a polyethylenepolyamine.

3. The method of claim 2, wherein said polyfunctional amine is ammonia.

4. The method of claim 2, wherein said polyfunctional amine is a primary amine.

5. The method of claim 4, wherein said primary amine is a lower alkyl amine, said alkyl group containing a maximum of three carbon atoms.

6. The method of claim 5, wherein said lower alkyl amine is methylamine.

7. The method of claim 2, wherein the polyfunctional amine is an alkylene diamine.

8. The method of claim 7, wherein said alkylene diamine is selected from the group consisting of ethylene diamine, propylene diamine, butylene diamine, and dimethylaminopropylamine.

9. The method of claim 8, wherein said alkylene diamine is ethylene diamine.

10. The method of claim 8, wherein said alkylene diamine is dimethylaminopropylamine.

11. The method of claim 2, wherein said polyethylenepolyamine is selected from the group consisting of diethylenetriamine, triethylenetetramine, and tetraethylenepentamine.

12. The method of claim 1, wherein the microorganisms are present in an aqueous system.

13. The method of claim 12, wherein the aqueous system is selected from the group consisting of fresh water, cooling water and swimming pool water.

14. The method of claim 13, wherein the concentration of said composition in said aqueous system is about 0.5 to about 500 parts per million (w/w).

15. The method of claim 1, wherein said microorganisms comprise a bacterial species.

16. The method of claim 1, wherein said microorganisms comprise an algal species.

* * * * *